United States Patent [19]
Alper

[11] 3,936,527
[45] Feb. 3, 1976

[54] TREATMENT OF PETS
[75] Inventor: Conrad Hugh Alper, East Rockaway, N.Y.
[73] Assignee: Damon Corporation, Needham Heights, Mass.
[22] Filed: Mar. 21, 1974
[21] Appl. No.: 453,211

Related U.S. Application Data
[63] Continuation of Ser. No. 886,725, Dec. 19, 1969, abandoned.

[52] U.S. Cl. .................................. 424/177; 424/319
[51] Int. Cl.² ......................................... A61K 37/00
[58] Field of Search ............................ 424/177, 319

[56] References Cited
UNITED STATES PATENTS
3,087,857   4/1963   Davis et al. ........................ 424/57 X OTHER PUBLICATIONS
Veterinary Drug Encyclopedia, 9th Edition, 1961, pp. 43, 73, 133, 137, 143, 182, and 195.

Primary Examiner—Norman A. Drezin
Attorney, Agent, or Firm—Kenway & Jenney

[57]   ABSTRACT
Treatment of dogs and cats to overcome mouth odors by feeding tablets rich in methionine.

7 Claims, No Drawings

TREATMENT OF PETS

This application is a continuation of my copending application Ser. No. 886,725 filed Dec. 19, 1969, now abandoned.

This invention relates to the prevention of mammalian mouth odors.

The causes of the annoying strong mouth odors of some pet dogs are not clearly understood. The treatments generally used for this condition have not solved the problem. Among such suggested treatments are regular cleaning of teeth and removal of tartar and even dental surgery, changes in diet, giving bones to chew, dosing with chlorophyll preparations or with powders that foam in the mouth or with charcoal tablets. A similar mouth odor problem is also encountered with cats.

It has now been found, surprisingly, that a very large proportion of cases of strong mouth odors of dogs and cats can be treated successfully in a simple manner, by feeding the animals with tablets rich in methionine. The treatment has been successful not only for cases in which the attending veterinarian has attributed the breath odor to impaired digestion but also in cases which the veterinarian has diagnosed the breath odor as being due to oral conditions such as dental tartar, gingivitis or ulcerations of the mouth.

The following Example is given to illustrate this invention further. In this application all proportions are by weight unless otherwise specified.

EXAMPLE

Tablets were prepared, each containing 200 mg of d,l-methionine, 243 mg of soya protein (Promine D), 300 mg of dessicated liver, 45 mg of dry fish meal, 12 mg of dry yeast, 35 mg of sorbitol, 11 mg of acacia, 17 mg of polyethylene glycol 6000 (average molecular weight 6000-7500), 7.5 mg of magnesium stearate and 15 mg of stearic acid. The soya protein, dessicated liver, fish meal and yeast help to make the tablets more palatable and acceptable to the animal. The acacia, polyethylene glycol and sorbitol serve as excipients, while the magnesium stearate and stearic acid are lubricants (e.g. to help in the conventional tablet pressing operation). The tablets were hard and of conventional round, squat, cylindrical shape with convex ends (like conventional aspirin tablets), they crumbled when chewed without substantially adhering to the teeth; they can also be crumbled by hand. They were made by mixing the powdered ingredients and compressing them together in a conventional tablet-forming machine.

In a test the tablets were fed to dogs and cats having chronic cases of annoying strong mouth odors (which had been diagnosed as due to dental tartar, gingivitis, ulcerations and impaired digestive function) at a dosage of 1 to 2 tablets daily for animals weighing 5 to 20 pounds, 2 to 3 tablets daily for animals weighing 20 to 50 pounds and 3 tablets daily for animals weighing 50 pounds and over. The tablets were fed directly to the mouths of the animals by hand or crumbled and placed in the animal's food. Excellent results were obtained, and in many cases a significant reduction in mouth odor was evident in a matter of 3 to 6 hours. It appears that the methionine acts systemically rather than topically in the mouth. A suitable maintenance dosage, after the first week of treatment, is one tablet daily for animals weighing 5 to 20 pounds, one to two tablets daily for those weighing 20 to 50 pounds, and two tablets daily for animals over 50 pounds in weight.

It will be seen that the initial dosage used is generally in the range of some 10 to 50 mg of the methionine per pound of body weight. From a practical point of view, it is preferred that each tablet contain over 50 mg, and more preferably over 100 mg, of the methionine. Much larger amounts than 200 mg per tablet are believed to be unnecessary and possibly wasteful, and for practical purpose it is preferred that the methionine content be less than 500 mg, and more preferably less than 400 mg, per tablet. Generally the tablets will contain at least 5% methionine.

The Promine D is a sodium soy proteinate containing 95% protein on a dry basis and about 90% protein on an as is basis, about 4.5% ash and about 0.2% fibre having a pH of 7; the amino acid composition of this soy protein, in terms of grams amino acid per 100 grams protein, is arginine 7.6, cystine 1.0, histidine 2.5, isoleucine 4.7, leucine 7.7, lysine 6.0, methionine 1.1, phenylalanine 5.3, threonine 3.6, tryptophan 1.4, tyrosine 3.7, valine 4.7.

It is understood that the foregoing detailed description is given merely by way of illustration and that variations may be made therein without department from the spirit of the invention. The "Abstract" given above is merely for the convenience of technical searchers and is not to be given any weight with respect to the scope of the invention.

I claim:

1. A method of alleviating strong mouth odor in a dog or cat having said odor which comprises feeding said dog or cat an effective amount of methionine to reduce said odor.

2. The method of claim 1 in which said amount of methionine is in tablet form.

3. The method of claim 2 wherein the methionine content per tablet is over 50 mg.

4. The method of claim 3 wherein each tablet contains about 50–500 mg. of methionine.

5. The method of claim 3 wherein the tablets further contain protein concentrates.

6. The method of claim 5 wherein the protein concentrates comprise a blend of soya protein, dessicated liver and fish meal.

7. A method of alleviating strong mouth odor in a dog or cat having said odor which comprises feeding said dog or cat a tablet containing at least 5% methionine in a daily dosage of 10 to 50 mg of methionine per pound of body weight in addition to its regular diet.

* * * * *